United States Patent [19]
Hamuro et al.

[11] Patent Number: 6,060,449
[45] Date of Patent: May 9, 2000

[54] NEOVASCULARIZATION INHIBITOR CONTAINING TISSUE FACTOR PATHWAY INHIBITOR

[75] Inventors: Tsutomu Hamuro, Kumamoto; Yo Nakahara, Kumamoto-ken; Sumiyo Takemoto, Kumamoto; Seiji Miyamoto, Kumamoto-ken, all of Japan

[73] Assignee: Juridical Foundation The Chemo-Sero-Therapeutic Research Institute, Kumamoto-ken, Japan

[21] Appl. No.: 09/142,479

[22] PCT Filed: Mar. 24, 1997

[86] PCT No.: PCT/JP97/00973

§ 371 Date: Sep. 10, 1998

§ 102(e) Date: Sep. 10, 1998

[87] PCT Pub. No.: WO97/35609

PCT Pub. Date: Oct. 2, 1997

[30] Foreign Application Priority Data

Mar. 25, 1996 [JP] Japan ................................. 8-096176

[51] Int. Cl.$^7$ .......................... A61K 38/02; A61K 38/16; A61K 38/55
[52] U.S. Cl. ................... 514/12; 514/2; 514/21; 514/885; 514/886; 514/914; 514/8; 424/158.1; 530/388.25
[58] Field of Search .................... 514/12, 21, 8, 514/885, 886, 914; 424/158.1; 530/388.25

[56] References Cited

U.S. PATENT DOCUMENTS 5,276,015  1/1994  Khouri et al. ............................ 514/12
5,902,582  5/1999  Hung .................................... 424/130.1

FOREIGN PATENT DOCUMENTS 7-79774   3/1995  Japan .
9709063   3/1997  WIPO .

OTHER PUBLICATIONS

Hambrough et al "Tissue Factor Pathway Inhibitor (TFPI) is an Inhibitor of Angiogenesis" Proceedings of the American Cancer Association for Cancer Research, vol. 40 : 68 #451, 1999.
Hambrough et al., Control of Tumor Growth in Animals by Infusion of an Angiogenesis Inhibitor, Proc. Natl. Acad. Sci. USA, vol. 77, No. 7, 4331–4335, 1980.
McCulloch, P., et al., "Association Between Tumor Angiogenesis and Tumor Cell Shedding into Effluent Venous Blood During Breast Cancer Surgery," *The Lancet* 346:1335–1335 (1995).
Folkman, J., et al., "Angiogenic Factors," *Science* 235:442–447 (1987).
Folkman, J., et al., "Angiogenesis," *The Journal of Biological Chemistry* 267–$_{16}$ 10931–10934 (1992).
Connolly, D.T., et al., "Tumor Vascular Permeability Factor Stimulates Endothelial Cell Growth and Angiogenesis," *Journal of Clinical Investigation* 84:1470–1478 (1989).
Taylor, S. et al., "Protamine is an Inhibitor of Angiogenesis," *Nature* 297:307–312 (1982).
Bronze, G.J., et al., "Isolation of the Tissue Factor Inhibitor Produced by HepG2 Hepatome Cells," *Proc. Natl. Acad. Sci. USA* 84:1886–1890 (1987).
Wun, T.–C., et al., "Cloning and Characterization of a cDNA Coding for the L$_{ip}$oprotein–associated Coagulation Inhibitor Shows That Is Consists of Three Tandem Kunitz–type Inhibitory Domains," *J. Biochem.* 263:6001–6004 (1988).
Kamei, S., et al., "Amino Acid Sequence and Inhibitory Activity of Rhesus Monkey Tissue Factor Pathway Inhibitor (TFPI): Comparison with Human TFPI," *Journal of Biochemistry* 115:708–714 (1994).
Wesselschmidt, R.L., et al., "cDNA Sequence of Rabbit Lipoprotein–associated Coagulation Inhibitor," *Nucleic Acids Research* 18–21:6440 (1990).
Warn–Cramer, B.J., et al., "cDNA Sequence of Rabbit Tissue Factor Pathway Inhibitor," *Nucleic Acids Research* 20–13:3548 (1992).
Enjyoji, K., et al., "cDNA Cloning and Expression of Rat Tissue Factor Pathway Inhibitor (TFPI)," *Journal of Biochemistry* 111:681–687 (1992).
Enjyoji, K., et al., "Effect of Heparin on the Inhibition of Factor Xa by Tissue Factor Pathway Inhibitor: A Segment, Gly212–Phe243, of the Third Kunitz Domain Is a Heparin–Binding Site," *Biochemistry* 34–17:5725–5735 (1995).
"Medicine Today," 49 (5), p. 927 (1994).

*Primary Examiner*—F. T. Moezie
*Attorney, Agent, or Firm*—Browdy and Neimark

[57] ABSTRACT

There is provided an inhibitor of angiogenesis induced by growth of the vascular endothelial cells that comprises Tissue Factor Pathway Inhibitor (TFPI) as an active ingredient. The TFPI-containing preparation of the present invention can effectively inhibit angiogenesis induced by growth of the vascular endothelial cells, and thus, is quite efficacious for preventing and treating the conditions of diseases associated with angiogenesis such as malignant tumors.

13 Claims, 3 Drawing Sheets

NEOVASCULARIZATION INHIBITOR CONTAINING TISSUE FACTOR PATHWAY INHIBITOR

CROSS-REFERENCE TO RELATED APPLICATIONS

This application is a 371 national stage application of PCT/JP97/00973, filed Mar. 24, 1997.

BACKGROUND OF THE INVENTION

1. Field of the Invention

The present invention relates to an agent for suppressing growth of the vascular endothelial and an inhibitor of angiogenesis induced by growth of the vascular endothelial cells which comprises Tissue Factor Pathway Inhibitor (TFPI) as active ingredient. More particularly, the present invention relates to a TFPI-containing preparation for prevention and treatment of angiogenic diseases through effective inhibition of angiogenesis induced by growth of the vascular endothelial cells.

2. Description of the Related

Angiogenesis is growth of new blood vessels, especially capillary vessels. Although angiogenesis is a significant physiological event for developing embryos or growing individuals, it is widely known that angiogenesis mostly detrimentally affects healthy adults and is only favorable to healing of wounds or menstrual cycle. In case of malignant tumors, for example, growth of the vascular endothelial cells or angiogenesis of capillary vessels is essential to development of tumor tissue. It is considered this is because the tumor cells produce and secrete a growth factor necessary for angiogenesis, and as a result, the vascular endothelial cells are stimulated to divide and propagate towards the tumor site. Accordingly, inhibition of angiogenesis can be a means to control growth of malignant tumors.

For treating malignant tumors, surgical enucleation of the tumors has been conducted. However, if any one of tumor cells fails to be removed but remains in the affected part after enucleation of the tumors, relapse of the tumor occurs. Moreover, it is reported that tumor cells appearing in blood flow increase during or after surgical nucleation of tumor tissue where angiogenesis is highly developed, implicating an increased risk of metastasis to other organs [McCulloch, P. et al., *The Lancet,* 346, p1334 (1995)]. In case of such a surgical enucleation of tumor tissue, the use of an angiogenic inhibitor that can inhibit angiogenesis will permit prevention of relapse at the primary focus and growth of metastasized tumor cells and hence can be a means for treating malignant tumors.

In addition to propagation of malignant tumors, there are known various diseases induced by angiogenesis, including the so-called angiogenic diseases such as diabetic retinopathy, retrolental fibroplasia, neovascular glaucoma, psoriasis, angiofibroma, immune and nonimmune inflammation (including rheumatic arthritis), propagation of capillary vessels in arteriosclerosis plaques, angioma and Kaposi's sarcoma [Folkman, J. et al., *Science,* 235, p442 (1987)]. One can well expect that inhibition of angiogenesis could treat these diseases.

It has been confirmed that the growth of endothelial cells of blood vessel is much significant in the mechanism of angiogenesis. That is, angiogenesis occurs in the following mechanism: (i) the basement membrane of the existing blood vessels is first degraded by the action of a proteolytic enzyme and then the endothelial cells are released out of the locally destroyed membrane, (ii) the released endothelial cells migrate into the extravascular area where they proliferate through cell division, (iii) after the proliferation, they gradually differentiate into the tube-like structure and a new blood vessel is then formed, and (iv) finally the new blood vessel is combined together to complete angiogenesis [Folkman, J. et al., *J.Biol.Chem.,* 267, p10931 (1992)]. As a promoting factor of angiogenesis, there are known peptidic substances, acidic Fibroblast Growth Factor (aFGF) and basic Fibroblast Growth Factor (bFGF), which induce angiogenesis through acceleration of release and growth of the vascular endothelial cells. Recently, a vascular endothelial growth factor/vascular permeability factor (VEGF/VPF), which is a growth factor specific for the vascular endothelial cells, was found as a new promoting factor of angiogenesis [Ferrara, N. et al., *J.Clin.Invest.,* 84, p1470 (1989)].

There are known several compounds that exhibit inhibition against growth of the vascular endothelial cells. Among them is protamine, which is a protein of a molecular weight 4,300 that occurs only in sperm and is abundant in a basic amino acid arginine. The hitherto experiments confirmed that protamine inhibits growth of tumors through inhibition of angiogenesis of tumors based on its heparin-binding ability [Taylor, S. et al., *Nature,* 297, p307 (1982)]. However, protamine is known to be antigenic in humans and to induce anaphylactic reaction on and after the second administration. Due to this toxicity, it is difficult to frequently use protamine in humans. Accordingly, there have been vastly investigated substances that are effective as an inhibitor of growth of the vascular endothelial cells and angiogenesis but are not toxic in humans. However, at present, compounds that exhibit both the effective activity to inhibit angiogenesis and safety in humans have not yet been found.

SUMMARY OF THE INVENTION

The present inventors have searched for substances having an activity to inhibit growth of cultured human vascular endothelial cells in order to find out an agent capable of preventing or treating various angiogenic diseases such as malignant tumors through inhibition of growth of the vascular endothelial cells and angiogenesis. As a result, the present inventors have found that Tissue Factor Pathway Inhibitor (hereinafter referred to as "TFPI") has a quite novel activity to quite effectively inhibit growth of the vascular endothelial cells and thus completed the present invention based on this finding. That is, the present invention relates to an agent for suppressing growth of the vascular endothelial and an inhibitor of angiogenesis induced by growth of the vascular endothelial cells which comprises TFPI as an active ingredient. Administration of an effective amount of said agent or inhibitor can effectively prevent or treat malignant tumors or other angiogenic diseases. Since human TFPI occurs intrinsically within the human body, it can be used safely without exhibiting antigenicity even if it is administered externally. TFPIs derived from other mammals having substantial homology with human TFPI can also be used safely without exhibiting antigenicity. Also, TFPI not only can prevent angiogenesis from abnormally progressing but also can promote regression of blood vessels that have already been formed.

DETAILED DESCRIPTION OF THE INVENTION

Figure 1:
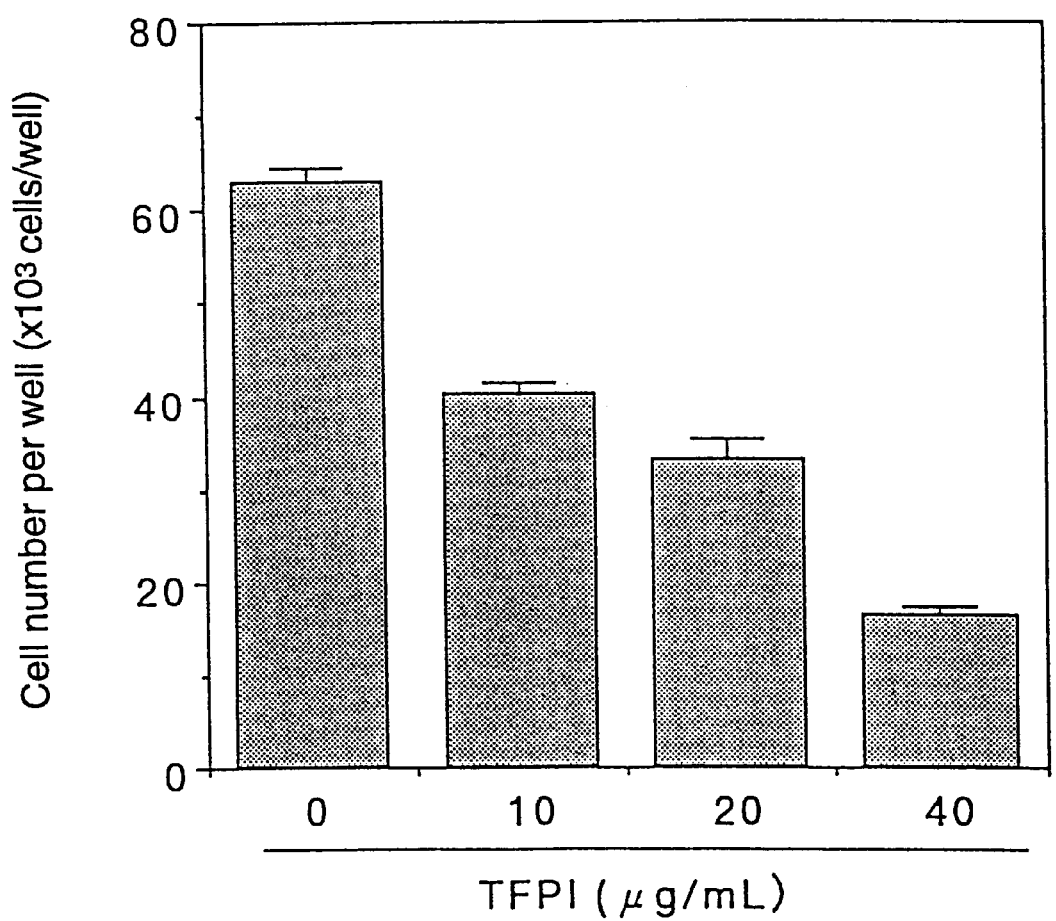
FIG. 1 shows an inhibitory activity of TFPI on growth of the vascular endothelial cells.

TFPI is a glycoprotein occurring within the living body known to have an activity to inhibit the external blood coagulation reaction [Broze, G. J., Proc.Natl.Acad.Sci. (USA), 84, p1886 (1987)]. TFPI consists of several domains, including a region being abundant in an acidic amino acid (hereinafter referred to as "N-terminal region"), three structural regions of so-called Kunitz domain (hereinafter referred to as "Kunitz 1", "Kunitz 2" and "Kunitz 3" from the amino-terminal in this order), and a region of 27 amino acid residues being abundant in a basic amino acid at the C-terminal (hereinafter referred to as "C-terminal region"), from the amino-terminal in this order. The Kunitz 1 region binds to one of blood coagulation factors, the activated factor VII, to neutralize its protease activity, whereas the Kunitz 2 region binds to another blood coagulation factor, the activated factor X, to neutralize its protease activity. It is believed that these activities together are responsible for effective inhibition of the blood coagulation reaction at the early stage. It is not yet known as to whether the N-terminal region exhibits any significant physiological activity. However, the C-terminal region is known to strongly bind to glycosaminoglycan with a negative charge, especially heparin. Human TFPI consists of 276 amino acid residues and has a molecular weight of about 42,000.

An amino acid sequence of TFPI has been reported for humans [Wun, T.-C. et al., J.Biol.Chem., 263, p6001 (1988)], for monkeys [Kamei et al., J.Biochem., 115, p705 (1994)], homology with humans being 94%, for rabbits [Wesselschmidt, R. L. et al., Nuc.Acids Res., 18, p6440 (1990); Warn-Cramer, B. J. et al., Nuc.Acids Res., 20, p3548 (1992)], homology with human TFPI being 72%, for rats [Enjyoji, K. et al., J.Biochem., 111, p681 (1992)], homology with human TFPI being 56%, and the like.

TFPI for use as an active ingredient in the suppressor of growth of the vascular endothelial cells and the inhibitor of angiogenesis of the present invention may be either native TFPI from blood or cultured cells derived from mammals including humans or a recombinant TFPI prepared by the genetic recombination technique from mammals including humans. The present invention also encompasses a derivative of TFPI that has deletion, substitution, insertion or addition of one or more amino acid residues in the amino acid sequence of TFPI and has a physiological activity equivalent to that of native TFPI obtained from blood or cultured cells or a recombinant TFPI prepared by the genetic recombination technique as far as it exhibits an activity to suppress growth of the vascular endothelial cells or an activity to inhibit angiogenesis. Specifically, as described in the following Examples, it has been found that C-terminal-deleted TFPI (TFPI−C), being completely deprived of 27 amino acid residues of the C-terminal region of TFPI, significantly exhibits an activity to suppress growth of the vascular endothelial cells and an activity to inhibit angiogenesis likewise full-length TFPI (TFPI+C) and such C-terminal-deleted TFPI can also be used as TFPI in the present invention. Since the suppressor of growth of the vascular endothelial cells and the inhibitor of angiogenesis of the present invention are administered to humans, the active ingredient TFPI is preferably derived from humans in order to obviate an immune response and for assurance of safety.

A process for preparing TFPI of the present invention is not particularly limited but includes an isolation and purification from blood or cultured cells obtained from mammals such as humans and production by the genetic recombination technique. However, TFPI is preferably prepared by the genetic recombination technique since it is difficult to produce a large amount of TFPI by isolation and purification of TFPI from blood due to a quite low TFPI level in blood (about 100 ng/mL).

The suppressor of growth of the vascular endothelial cells and the inhibitor of angiogenesis of the present invention comprises TFPI as an active ingredient and an appropriate pharmaceutically acceptable carrier (gelatin sponge and the like) or an excipient (human serum albumin, sugars, and the like) depending on an object of treatment or actual indication. A specific dosage form preferably includes, but is not limited to, a solution prepared by dissolving a dry formulation comprising a mixture of TFPI, an appropriate known excipient (human serum albumin, sugars, etc.), a stabilizer (an amino acid etc.) and a buffer (citric acid etc.) in water for injection. For storage of TFPI, it is preferably stored with sealing in a dry state using a lyophilization etc. so that the efficacy of TFPI is maintained to a maximum degree. In that case, TFPI may be stored in admixture with an appropriate known excipient or stabilizer.

An administration route of the TFPI-containing preparation of the present invention is not particularly limited. For example, TFPI can be administered by directly applying a TFPI dissolved in a suitable sterile aqueous medium into the affected tissue during operation, by applying the solution to the surface of or around the affected part, or by injecting the solution intravenously, subcutaneously, intradermally or intramuscularly through bolus or continuous administration. TFPI may also be administered with eye drops. Alternatively, TFPI powder without dissolution may also be administered directly to the affected part. Furthermore, TFPI may also be administered by directly introducing a suitable expression vector, wherein a gene engineered to express TFPI is incorporated, to the affected tissue where TFPI is overexpressed. TFPI may also be administered in combination with another medicaments such as an anticancer agent, an immunosuppressant, an antiinflammatory agent, an agent for treating diabetes mellitus, an antibiotic, etc.

An effective amount of the active ingredient TFPI of the suppressor of growth of the vascular endothelial cells and the inhibitor of angiogenesis of the present invention may vary depending on the route or way of administration but is preferably in an amount sufficient for providing a blood level of TFPI ranging from 5 $\mu$g/ml to 80 $\mu$g/ml within angiogenesis.

The present invention is hereinbelow explained in more detail by means of Examples so that the present invention is more deeply understood but it is not limited to these Examples.

PREPARATION EXAMPLE

Preparation of TFPI

TFPI as used in the following Examples was purified from a culture supernatant of Chinese Hamster Ovary cell line, in which human TFPI cDNA was introduced, by affinity chromatography using anti-TFPI monoclonal antibody (HTFPI-K9; BIKOKEN KINKI 14467)-conjugated gel and heparin gel (Pharmacia-LKB) as described by Kamei et al. (Japanese Patent Publication No. 79774/1995) or Enjyoji [*Biochem.*, 34, p5725 (1995)]. The culture supernatant contains both full-length TFPI (TFPI+C) and C-terminal-deleted TFPI (TFPI–C). Both types of TFPI may be isolated and purified by affinity chromatography using heparin gel with NaCl gradient elution. The thus obtained full-length TFPI (TFPI+C) and C-terminal-deleted TFPI (TFPI–C), being deprived of the N-terminal 27 amino acid residues of TFPI, were investigated in the following Examples.

EXAMPLE 1

Inhibitory Effect of Full-length TFPI on Growth of Human Vascular Endothelial Cells For endothelial cells, human umbilical cord vein endothelial cells (HUVEC) were purchased from KURABO INDUSTRIES LTD and used at the third passage. For a growth medium, E-GM medium (modified MCDB131 medium comprising 2% fetal bovine serum, 10 ng/ml human epidermal growth factor, 1 $\mu$g/ml hydrocortisone, 0.4% calf brain extract, 10 $\mu$g/ml heparin, and an antibacterial agent; manufactured by KURABO INDUSTRIES LTD) was used.

The endothelial cells suspended in E-GM medium were inoculated into a 48-well culture plate (manufactured by Iwaki Glass K.K.) at a cellular density of 2,500 cells/well and incubated at 37° C. in a $CO_2$ incubator. Two days after inoculation, the culture medium was replaced with fresh E-GM medium containing full-length TFPI (TFPI+C) at various concentrations (0, 10, 20, and 40 $\mu$g/ml). Thereafter, culture was continued while replacing with the fresh medium at intervals of every 2 days. The culture medium was used at an amount of 0.3 ml per well. Six days after inoculation, the cells grown on the plate were detached by the treatment with a trypsin/EDTA solution in a conventional manner and a cell count per well was measured with a Coulter counter (manufactured by Coulter).

FIG. 1 is a graph showing a mean value and a standard deviation of a cell count with each group comprising 3 wells. The addition of TFPI significantly (Student's t-test, effective level 1%) inhibited growth of the vascular endothelial cells in a concentration-dependent manner.

EXAMPLE 2

Inhibitory Effect of Full-length TFPI and C-terminal-deleted TFPI on Growth of Human Vascular Endothelial Cells Inhibitory effect on growth of human vascular endothelial cells was investigated for C-terminal-deleted TFPI (TFPI–C) wherein a heparin-binding region of full-length TFPI (TFPI+C), the C-terminal basic amino acid sequence (27 amino acids), is deprived.

The endothelial cells suspended in a growth medium E-GM were inoculated into a 48-well culture plate at a cell density of 2,500 cells/well and cultured in a $CO_2$ incubator at 37° C. Two days after inoculation, the culture medium was replaced with fresh E-GM medium containing full-length TFPI (TFPI+C) or C-terminal-deleted TFPI (TFPI–C) at various concentrations (0, 5, 10, 20, 40, and 80 $\mu$g/ml). Thereafter, culture was continued while replacing with the fresh medium at intervals of every 2 days. The culture medium was used at an amount of 0.3 ml per well. Six days after inoculation, the cells grown on the plate were detached by the treatment with a trypsin/EDTA solution in a conventional manner and a cell count per well was measured with a Coulter counter (manufactured by Coulter).

Figure 2:
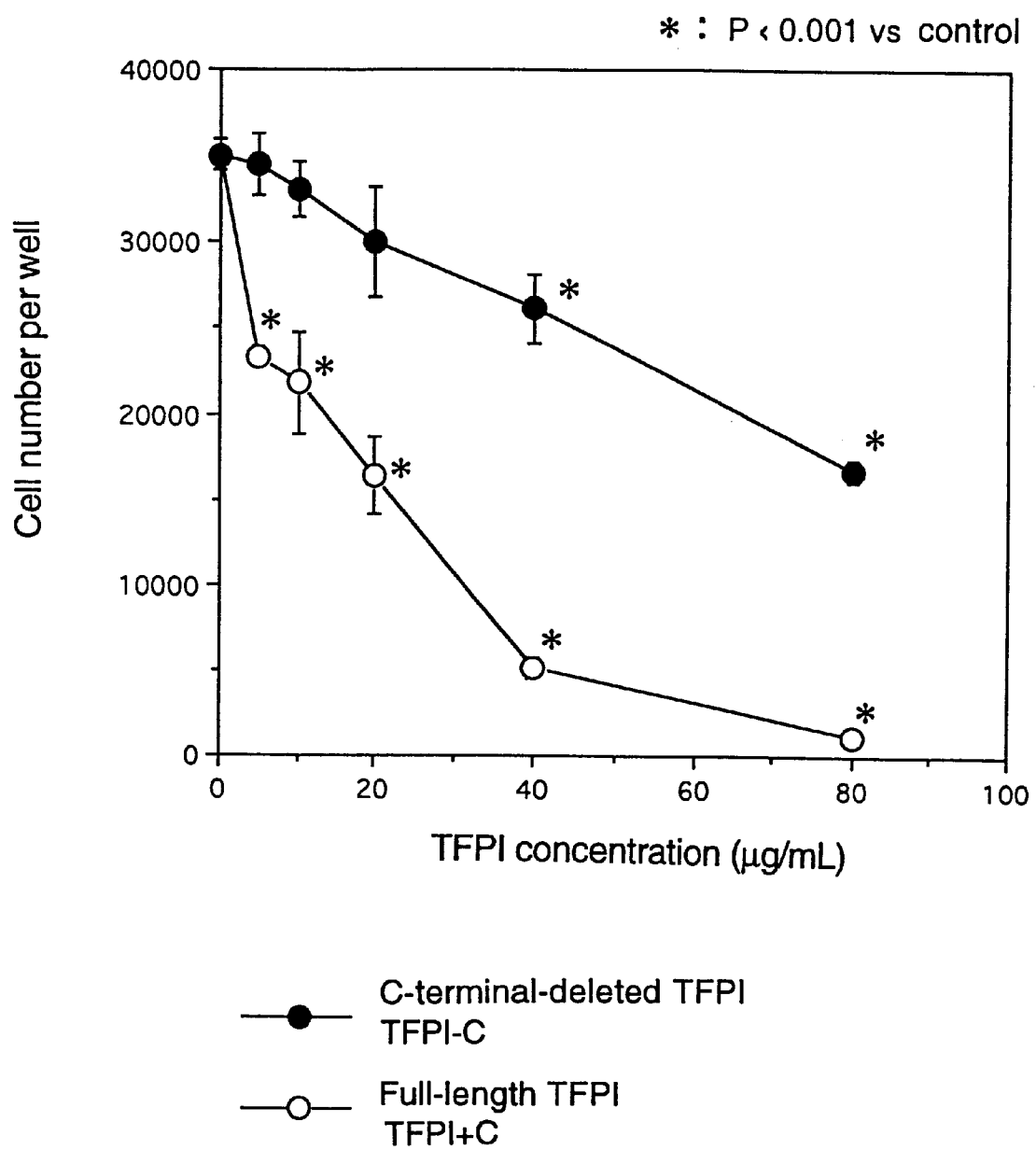
FIG. 2 shows an inhibitory activity of full-length TFPI (TFPI+C) and C-terminal-deleted TFPI (TFPI−C) on growth of the vascular endothelial cells.

FIG. 2 is a graph showing a mean value and a standard deviation of a cell count of the groups added with full-length TFPI (TFPI+C) or C-terminal-deleted TFPI (TFPI–C) (with each group comprising 4 wells). As a result, it was found that both types of TFPI significantly (Student's t-test, effective level 1%) inhibited growth of the vascular endothelial cells in a concentration-dependent manner, and thus, even non full-length TFPI could inhibit growth of the endothelial cells.

EXAMPLE 3

Effect of TFPI on Growth-arrested Vascular Endothelial Cells

The vascular endothelial cells were cultured on a culture medium free from a growth factor [a basal medium HuMedia-EB (manufactured by KURABO INDUSTRIES LTD) supplemented with 2% fetal bovine serum and an antibacterial agent] and the effect of TFPI under conditions where no cell growth occurs was investigated.

The endothelial cells suspended in the medium without addition of a growth factor were inoculated into a 48-well culture plate at a cell density of 10,000 cells/well and cultured in a $CO_2$ incubator at 37° C. Two days after inoculation, the culture medium was replaced with the same fresh medium containing full-length TFPI (TFPI+C) or C-terminal-deleted TFPI (TFPI–C) at various concentrations (0, 5, 10, 20, 40, and 80 $\mu$g/ml). Thereafter, the cells were cultured for additional 2 days and, after the cells grown on the plate were detached by the treatment with a trypsin/EDTA solution, a cell count per well was measured with a Coulter counter.

Figure 3:
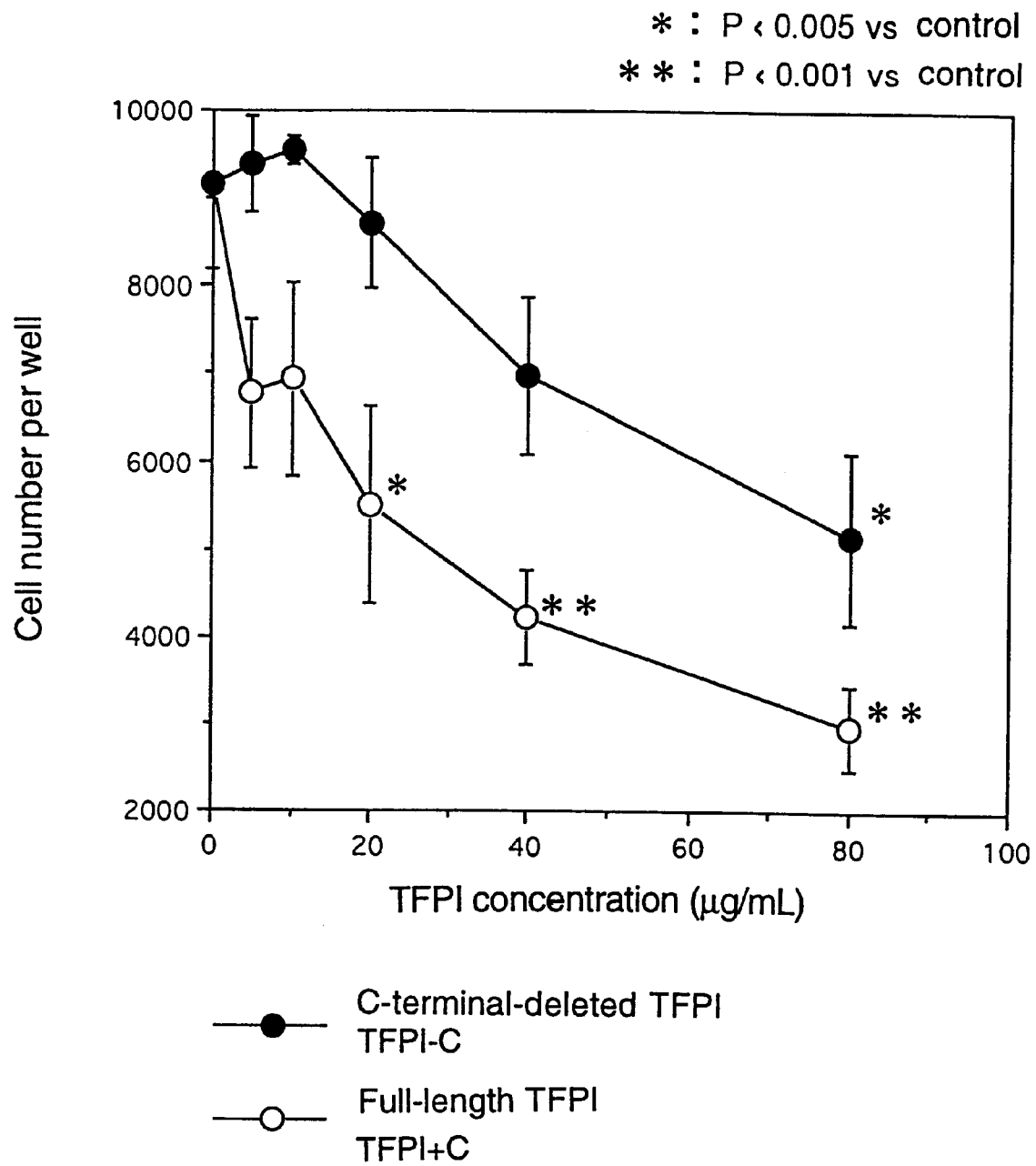
FIG. 3 shows an effect of TFPI on the growth-arrested vascular endothelial cells.

FIG. 3 shows a relationship between the concentration of TFPI and the cell count on the plate with each group comprising 4 wells wherein the cell count was indicated as a mean value and a standard deviation. As a result, both types of TFPI significantly (Student's t-test, effective level 1%) inhibited growth of the vascular endothelial cells in a concentration-dependent manner.

These results prove that TFPI not only inhibits growth of the endothelial cells but also blocks the action of the growth-arrested endothelial cells. That is, it was shown that TFPI not only could prevent angiogenesis from abnormally progressing but also could possibly promote recession of angiogenesis that has already been formed.

We claim:

1. A method for preventing or treating angiogenic diseases induced by growth of vascular endothelial cells in a patient in need of said therapy, comprising administering to said patient an amount sufficient for said therapy of Tissue Factor Pathway Inhibitor.

2. The method of claim 1, wherein said angiogenic disease is a malignant tumor, diabetic retinopathy, retrolental fibroplasia, neovascular glaucoma, psoriasis, angiofibroma, immune or nonimmune inflammation, propagation of capillary vessels in arteriosclerosis plaques, angioma, or Kaposi's sarcoma .

3. The method of claim 2, wherein said angiogenic disease is a malignant tumor.

4. The method of claim 2, wherein said angiogenic disease is diabetic retinopathy.

5. The method of claim 2, wherein said angiogenic disease is retrolental fibroplasia.

6. The method of claim 2, wherein said angiogenic disease is neovascular glaucoma.

7. The method of claim 2, wherein said angiogenic disease is psoriasis.

8. The method of claim 2, wherein said angiogenic disease is angiofibroma.

9. The method of claim 2, wherein said angiogenic disease is propagation of capillary vessels in arteriosclerosis plaques.

10. The method of claim 2, wherein said angiogenic disease is angioma.

11. The method of claim 2, wherein said angiogenic disease is Kaposi's sarcoma.

12. The method of claim 2, wherein said angiogenic disease is an immune or nonimmune inflammation.

13. The method of claim 12, wherein said immune or nonimmune inflammation is rheumatic arthritis.

* * * * *